United States Patent [19]

Attridge et al.

[11] Patent Number: 5,478,755

[45] Date of Patent: Dec. 26, 1995

[54] LONG RANGE SURFACE PLASMA RESONANCE IMMUNOASSAY

[75] Inventors: John W. Attridge, Bedford; Ian A. Shanks, Penn, both of England

[73] Assignee: Ares Serono Research & Development Ltd., Boston, Mass.

[21] Appl. No.: 198,642

[22] Filed: Feb. 17, 1994

Related U.S. Application Data

[63] Continuation of Ser. No. 469,543, May 23, 1990, abandoned.

[30] Foreign Application Priority Data

Jul. 25, 1988 [GB] United Kingdom ................ 8817710

[51] Int. Cl.$^6$ ........................ G01N 33/543; G01N 33/553
[52] U.S. Cl. ..................... 436/518; 356/317; 356/318; 356/445; 422/57; 422/82.05; 422/82.08; 422/82.11; 435/808; 436/164; 436/165; 436/172; 436/525; 436/527; 436/805
[58] Field of Search .................... 356/317, 318, 356/369, 445; 385/37; 422/57, 58, 82.05, 82.08, 82.11; 435/808; 436/164, 165, 172, 518, 525, 527, 805

[56] References Cited

U.S. PATENT DOCUMENTS

| | | | |
|---|---|---|---|
| 4,649,280 | 3/1987 | Holland et al. | 250/483.1 |
| 4,810,658 | 3/1989 | Shanks et al. | 356/246 |
| 4,815,843 | 3/1989 | Tiefenthaler et al. | 356/128 |
| 4,828,387 | 5/1989 | Sawyers et al. | 356/328 |
| 4,877,747 | 10/1989 | Stewart | 422/82.11 |
| 4,882,288 | 11/1989 | North et al. | 436/525 |
| 4,978,503 | 12/1990 | Shanks et al. | 422/102 |
| 4,997,278 | 3/1991 | Finlan et al. | 356/128 |
| 5,055,265 | 10/1991 | Finlan | 422/82.05 |

FOREIGN PATENT DOCUMENTS

| | | |
|---|---|---|
| 346016 | 3/1989 | European Pat. Off. . |
| 305109 | 12/1989 | European Pat. Off. . |
| 2185308 | 7/1987 | United Kingdom . |
| WO88/07202 | 9/1988 | WIPO . |

OTHER PUBLICATIONS

Quail et al, "Long Range Surface Plasmon Modes in Silver & Aluminum Films", Optics Letters, vol. 8, No. 7, 1983, pp. 377–379.

Brenner et al, "Angular Emission Profiles of Dye Molecules Excited by Surface Plasmon Waves at a Metal Surface", Optics Communications vol. 30 (2), 1979, pp. 145–149.

*Primary Examiner*—David A. Saunders
*Assistant Examiner*—Christopher L. Chin
*Attorney, Agent, or Firm*—Ostrolenk, Faber, Gerb & Soffen

[57] ABSTRACT

A method of assaying for a ligand in a sample involves incubating the sample in contact with a specific binding partner for the ligand carried on one surface of an optical structure, irradiating the structure at a suitable angle or range of angles to the normal such that the resonance and/or total internal reflection of the radiation occurs within the optical structure and/or the layer of specific binding partner, and analyzing the radiation in order to determine whether, and if desired the extent to which and/or rate at which the generated radiation and/or optical characteristics of the optical structure are altered by complex formation.

16 Claims, 8 Drawing Sheets

LONG RANGE SURFACE PLASMA RESONANCE IMMUNOASSAY

This is a continuation of application Ser. No. 07/469,543 filed on May 23, 1990 now abandoned.

This invention relates to assay techniques and to means for putting such techniques into effect. In particular it relates to an improved assay technique which provides an enhanced signal to noise ratio and enhanced sensitivity.

The assay techniques with which the present application is concerned are based on the affinity between the species which is to be assayed (hereinafter called "ligand") and a specific binding material for the ligand (hereinafter called "specific binding partner") which is coated on a particular type of surface. Such techniques are well known in the art, particularly in relation to coated optical structures whereby binding of the ligand to the specific binding partner results in a detectable change in the optical characteristics of said optical structure and have been described, for example, in EP-0112721 and EP- 0178083. The present invention provides an alternative method of assay with considerable advantages over the conventional assays.

In its broadest aspect, the invention is concerned with improvements to a method of assaying for a ligand in a sample which involves a) incubating the sample in contact with a specific binding partner for the ligand it is desired to detect carried on one surface of an optical structure;

b) irradiating another surface of the optical structure at a suitable angle or range of angles to the normal such that resonance and/or total internal reflection of the radiation occurs within the optical structure and/or the layer of specific binding partner; and c) analysing the reflected and/or generated radiation in order to determine whether, and if desired the extent to which and/or rate at which, the generated radiation and/or optical characteristics of the optical structure are altered by complex formation.

It is to be understood that the term generated radiation as used herein includes fluorescence and phosphorescence. Although the invention is described hereinafter with particular reference to fluorescence, it applies also to phosphorescence.

The optical structure comprises a substrate and optionally one or more layers of material interposed between said substrate and the layer of specific binding partner carried on the surface of said optical structure. Generally the layer of specific binding partner may be either continuous or discontinuous. However, in some embodiments of the invention as hereinafter described and in particular where the specific binding partner is carried directly on the substrate surface of the optical structure without any intervening layers of material therebetween, a continuous layer of specific binding partner may be preferred.

Unexpectedly, the method of the present invention has been found to be of general applicability for increasing the sensitivity of both direct and indirect sensing methods of assay based on the optical properties of certain surfaces. Direct sensing in the context of the present invention involves monitoring the modulation of a signal resulting from a biochemical reaction (e.g. antigen/antibody binding). Indirect sensing involves monitoring a label (e.g. a fluorophore) by a transducer in order to quantify a biochemical reaction.

The technique makes it possible to enhance substantially the intensity of the electric field at the surface of the optical structure thereby enhancing the interaction between the exciting radiation and the ligand/specific binding partner complex, so maximising the response to complex formation at the surface of the optical structure and, in those embodiments employing indirect sensing techniques, significantly reducing the background signal levels.

Thus, where a direct sensing method is used based on the change in refractive index of the surface layer carried on an optical structure upon binding of the ligand under assay, the method of the present invention may be applied to enhance the surface field intensity produced by the incident radiation source and to sharpen the resonance(s) associated with the coupling to modes which propagate in said surface layer.

Thus, in one aspect, the invention provides a method of assaying for a ligand in a sample which method comprises the steps of (a) incubating the sample in contact with a specific binding partner for the ligand it is desired to detect, the said specific binding partner being carried on one surface of an optical structure, said optical structure comprising a substrate and one or more layers of material interposed between said substrate and the said specific binding partner;

(b) irradiating another surface of said optical structure such that the radiation is totally internally reflected and resonance occurs within the optical structure, said resonance being either long-range surface plasmon resonance or resonant guided mode coupling; and (c) analysing the reflected radiation in order to determine whether, and if desired the extent to which and/or rate at which, the optical characteristics of the sensor formed by the optical structure and specific binding partner carried thereon are altered by formation of a complex between the ligand and the specific binding partner.

For example, in one embodiment of the invention the incident radiation may be coupled to a guided mode which can be supported by an optical structure of a particular geometry. Optical structures of suitable geometry have been previously disclosed in U.S. Pat. No. 4,649,280 in connection with a fluorescent immunoassay. However, it has not hitherto been appreciated that similar techniques could be applied to a direct sensing method of assay. Preferably, the optical structure comprises a transparent (at least at the wavelength of radiation used) substrate coated with a thin metal layer such as silver or gold, which metal layer is itself coated with a layer of dielectric material such as silica. The layer of dielectric material is of a thickness, for example of the order of a wavelength of the incident radiation used, sufficient to support one or more guided modes but it is particularly preferred to employ a thickness of dielectric material which will support only a single guided TE or TM mode. For example, for a substrate of refractive index 1.52 with a silver layer of 50 nm and an incident radiation wavelength of 543 nm, the thickness of a dielectric layer of silica for a single transverse magnetic (TM) guided mode is from 350 nm to 750 nm. A similar thickness is required to propagate a single guided mode of transverse electric (TE) radiation.

In an alternative direct sensing embodiment of the invention the incident radiation is coupled to a long-range surface plasmon mode which results from the interaction of surface plasmons on each side of the metal layer. In this embodiment the optical structure may, for example, comprise a glass substrate and the layer of metal, such as silver or gold, is displaced from the substrate by a layer of dielectric having a refractive index lower than that of the substrate, for example $MgF_2$. Long-range surface plasmon resonance (LRSPR) is conventionally associated with a geometry in which the refractive indices of the dielectric layers on each side of a metal layer are identical. However, we have found that LRSPR can still be achieved when there is a modest index mis-match and that a range of sensitivities are possible by using layers of differing thicknesses and/or by selecting materials of appropriately mismatched refractive index. Thus, if the dielectric layer thickness is decreased, the metal layer thickness needs to be increased to optimise resonance coupling between the incident radiation and the long-range surface plasmon.

The invention therefore further provides a sensor for detecting a ligand in a sample which comprises an optical structure having a substrate, a layer of metal and interposed therebetween a layer of dielectric material having a refractive index lower than that of said substrate, and a specific binding partner for the ligand it is desired to detect adsorbed on or bound to (directly or indirectly) the said metal layer, said layers being such that, in use, long range surface plasmon resonance may be propagated therein. Preferably the metal layer is of silver, 10–50 nm thick, more particularly 15.5 nm thick and the dielectric layer is of $MgF_2$ of 10–2000 nm thick, more particularly 1500 nm thick.

The sensitivity of direct sensing assays can be conveniently estimated from the resolution of the sensor. The resolution may be defined as the ratio of the angular shift in the resonance peak for a particular change in refractive index of the medium adjacent to the metal surface to the angular half width of the reflected resonance minimum. "Angular half width" as used herein means the angular range between those angles of incidence or reflectance, on either side of the angle of incidence or emergence associated with the resonance reflectance minimum at which the reflectance is at half its minimum value. The greater the resolution the greater is the sensitivity of the sensing system in resolving the changes in resonance due to ligand binding, hence improving the assay sensitivity. In comparable arrangements and for the same change in refractive index, the preferred materials and dimensions described in the first embodiment above give an r value of greater than 5 and those in the second embodiment above give an r value of greater than 12 (with an angular half width of about one sixth of a degree) compared to an r value of 0.47–0.76 and an angular half width of about 1.5 degrees using a bare silver film.

However, the method of the present invention is particularly advantageous when applied to an indirect sensing method of assay such as those techniques based on surface-bound fluorophores. As already described for the direct sensing techniques, the method may be used to enhance the surface field intensity produced by the incident radiation and to sharpen the resonance peaks produced. This in itself produces large improvements in the specificity and sensitivity of fluorescence assays because the bound fluorophores are excited by the evanescent field produced at the outer surface of the optical structure. This minimises excitation of unbound fluorophores and thus reduces background signal. In addition, the surface field intensity is greatly enhanced compared to both direct irradiation and evanescent irradiation via total internal reflection and thus the available energy is greater and the signal obtained from the bound fluorophore very significantly enhanced.

However, still further advantages can be obtained by coupling the emitted fluorescence to the detector via the optical structure and the angular range of the detector can be limited to ensure that substantially only that radiation emitted by the bound fluorophore is detected. Furthermore, by placing the detector outside the plane of irradiation/reflectance, a further decrease in the background signal may be achieved. Filtration of the detected light will then be required only to remove scattered, as opposed to reflected, excitation radiation. Suitable arrangements for the optical detectors to measure the fluorescence emission of bound fluorophores, coupled via total internal reflection or surface plasmon resonance into the optical structure, have been described in, for example, EP-0170376 and the use of evanescent field excitation using total internal reflection has also been disclosed in U.S. Pat. Nos. 4,608,344, 4,447,546 and 4,558,014. However, it has not previously been appreciated that the methods could be generally applicable, in a modified manner, alone or in combination, to provide substantial advantages over the prior art.

In another aspect, the invention provides a method of assaying for a ligand in a sample which method comprises the steps of (a) incubating the sample in contact with a specific binding partner for the ligand it is desired to detect, the s specific binding partner being carried on one surface of an optical structure and in the presence of a further reagent X being either a fluorescently or phosphorescently labelled ligand analogue specific for the same specific binding partner or a fluorescently or phosphorescently labelled further specific binding partner for the ligand it is desired to detect, said optical structure comprising a substrate and optionally one or more layers of material interposed between said substrate and the said specific binding partner;

(b) irradiating another surface of said optical structure in a plane perpendicular to the plane of the said layers of material and at a suitable angle or range of angles to the normal such that the radiation is totally internally reflected and such that fluorescence or phosphorescence is generated; and (c) monitoring the generated fluorescence or phosphorescence which emerges from an edge of said optical structure not in the path of the applied radiation and analysing said fluorescence or phosphorescence in order to determine whether, and if desired the extent to which and or rate at which, it is altered by complex formation.

For example, in one embodiment of the invention the evanescent field associated with total internal reflection can be used to excite fluorophores within about one micron of the optical structure—sample interface. The optical structure is irradiated with a single reflection in a plane substantially at right angles to the axis of the detection optics. This provides an advantage over the arrangements disclosed in the aforementioned US patents because the detected radiation and the source radiation are in different planes and thus resolution of incident and emitted radiation is simplified. Filtration of the detected light will be required only to remove scattered radiation, although such scattering of radiation emitted due to background solution fluorescence is substantially eliminated using evanescent excitation.

Examples of fluorescent molecules which are suitable for use as labels are rhodamine isothiocyanate, dansyl chloride, FITC and XRITC.

In a further aspect, the invention provides A method of assaying for a ligand in a sample which method comprises the steps of (a) incubating the sample in contact with a specific binding partner for the ligand it is desired to detect, the said specific binding partner being carried on one surface of an optical structure and in the presence of a further reagent X being either a fluorescently or phosphorescently labelled ligand analogue specific for the same specific binding partner or a fluorescently or phosphorescently labelled further specific binding partner for the ligand it is desired to detect, said optical structure comprising a substrate and one or more layers of material interposed between said substrate and the layer of specific binding partner carried on the surface of said optical structure;

(b) irradiating another surface of said optical structure at a suitable angle or range of angles to the normal such that resonance occurs within or at the surface of the optical structure, said resonance being surface plasmon resonance or long-range surface plasmon resonance and such that fluorescence or phosphorescence is generated; and (c) analysing the fluorescence or phosphorescence generated in order to determine whether, and if desired the extent to which and/or rate at which, it is altered by complex formation.

In a still further embodiment of the invention the incident radiation is coupled into a surface plasmon resonance (SPR) mode generated between a thin metal layer, for example of silver or gold, and a dielectric layer which may, for example, be of silica, phosphate glasses or a silane (e.g. glycidoxypropyltrimethoxysilane). Silica can act as a passivating layer to protect the metal from corrosion and to provide a surface on which the specific binding partner can be conveniently immobilised, for example, covalently. However, it will be appreciated that the specific binding partner may be directly adsorbed onto the metal layer to itself form the layer of dielectric material and in this particular embodiment it is preferred that said specific binding partner forms a continuous layer, at least over a discrete region of the optical structure. It has been shown that a surface plasmon's evanescent field intensity is greatly enhanced, compared to that associated with total internal reflection, due to the focussing effect of coupling the incident radiation to a two-dimensional surface wave. The surface field intensity attainable using surface plasmon resonance is wavelength dependent, being greater at longer wavelengths within the optimised optical structure.

Fluorophores within the evanescent field will be excited by a surface plasmon of the appropriate wavelength and enhanced emission will occur. Thus, the general advantages of enhanced surface field intensity and specificity of excitation are attained according to the method of the invention. However, these advantages can again be magnified greatly using a reciprocal optical arrangement whereby the excited fluorophore is able to return to the ground state by coupling its emission to a surface plasmon of the Stoke's shifted wavelength. In this embodiment, enhanced fluorescent emission will occur over a narrow range of angles governed by the surface plasmon dispersion and the fluorophore emission spectrum (see, for example, Bennet et al, Optics Communications 30, 145–149 (1979)). The subsequent radiation of the surface plasmon energy can then be detected by an optical arrangement similar to that described in EP-0170376 mentioned hereinbefore. As with evanescent irradiation alone, unbound solution fluorophore (i.e. fluorophore which is at a distance from the surface which is substantially greater than the wavelength of the incident radiation being used) can only be excited by the scattering of incident radiation but in view of the narrow angle of fluorescence emission of fluorophores within the evanescent field and the surface plasmon resonance properties of the metal film, any such solution signal will be still further attenuated by the metal film and hence the background signal further reduced.

The coupling probability of the excited fluorophore to the surface plasmons of the metal can be controlled by suitably spacing the specific binding partner layer away from the metal layer (see, for example, Weber and Eagan, Optics Letters 4, 236 (1979)).

In a still further embodiment of the invention the evanescent field associated with long range surface plasmon resonance is employed to excite surface-bound fluorophores. A sensor as described hereinbefore in which LRSPR may be propagated is suitable for use in such assays. In all respects the advantages of using LRSPR are the same as those previously discussed for surface plasmon resonance except that the surface field enhancement is greater (×10) than for surface plasmon resonance and the emission angles are narrower which is of particular advantage where the emitted light is itself coupled via LRSPR into the optical structure.

The methods of the present invention have become realistically attainable due to a number of modifications of the instrumentation required, both for irradiating the optical structure and for analysing the reflected, transmitted and/or propagated radiation. Thus, the present invention further provides apparatus suitable for use in a method of assay hereinbefore described which comprises (a)a sensor, the said sensor comprising a specific binding partner for a ligand it is desired to assay carried on the surface of an optical structure comprising a substrate and one or more layers of material interposed between said substrate and said specific binding partner; (b)a collimated source of radiation which is capable of being arranged such that, in use, the radiation enters said optical structure at an angle suitable to produce total internal reflection and optionally resonance (said resonance being surface plasmon resonance, long-range surface plasmon resonance or resonant guided mode coupling) within said optical structure; and (c) means for in use analysing reflected or generated radiation.

The radiation may be collimated, for example, to within one or two degrees and may, in use, be introduced into an optical structure positioned within said apparatus, for example, through an edge of the substrate of the optical structure or via a prism or a grating coupler. Ideally the source radiation is polarised, preferably transverse magnetic polarised, but an unpolarised radiation source may also be used.

Where the method of assay involves coupling the fluorescence of surface bound fluorophores into the optical structure, for example by total internal reflection, SPR or LRSPR, the sensitivity of the method may be further enhanced using apparatus wherein the angular range of view of the detector means is restricted, for example to about 3°, to correspond to the coupled fluorescence emission angles. A theoretical analysis of this effect is given in EP-0170376.

It is particularly preferred to apply the method of the invention to an immunoassay and in particular to use a specifically reactive sample collecting and testing device similar to that described in EP- 0171148, together with the method of optical analysis disclosed in EP-0170376. Thus, the present invention provides a specifically-reactive sample collecting and testing device possessing a cavity or cavities each having a dimension small enough to enable sample liquid to be drawn into the cavity by capillary action, and wherein at least one part of a wall of said cavity comprises a sensor for detecting a ligand in a sample, said sensor being of the type generally described herein. In this particular embodiment of the invention the optical structure comprises a planar waveguide.

In a preferred embodiment of such a device, the wall of the capillary cavity which is remote from the wall comprising a sensor carries in dry releasable form a fluorescently or phosphorescently labelled ligand analogue or a further specific binding partner.

However, it will be appreciated that the optical structure used in the method of assay according to the invention is not limited to planar waveguides and includes within its scope other optical structures such as gratings, prisms, optical fibres and slides, provided that a suitable geometry can be chosen for introducing the incident radiation other than via the sample and at a suitable angle or range of angles such that resonance and/or total internal reflection can occur.

In a preferred embodiment of the invention the ligand is an antigen and the specific binding partner comprises an antibody to the said antigen. However, the invention is not to be taken as limited to assays of antibodies or antigens. Examples of ligands which may be assayed by the method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinising hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, viruses such as influenza, parainfluenza, adeno-, hepatitis, respiratory and AIDS viruses, or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, goats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

The invention further provides a sensor for detecting a ligand in a sample by a method described hereinbefore which comprises an optical structure having a substrate coated with a thin layer of metal, which metal layer is itself coated with a layer of dielectric material of a thickness suitable to support one or more guided modes of radiation of wavelength employed when the sensor is in use and which dielectric layer carries a specific binding partner for the ligand it is desired to detect.

The following non-limiting Examples illustrate particular aspects of the invention.

EXAMPLES

EXAMPLE 1 Comparison of Resonance Excitation Geometries

Figure 1:
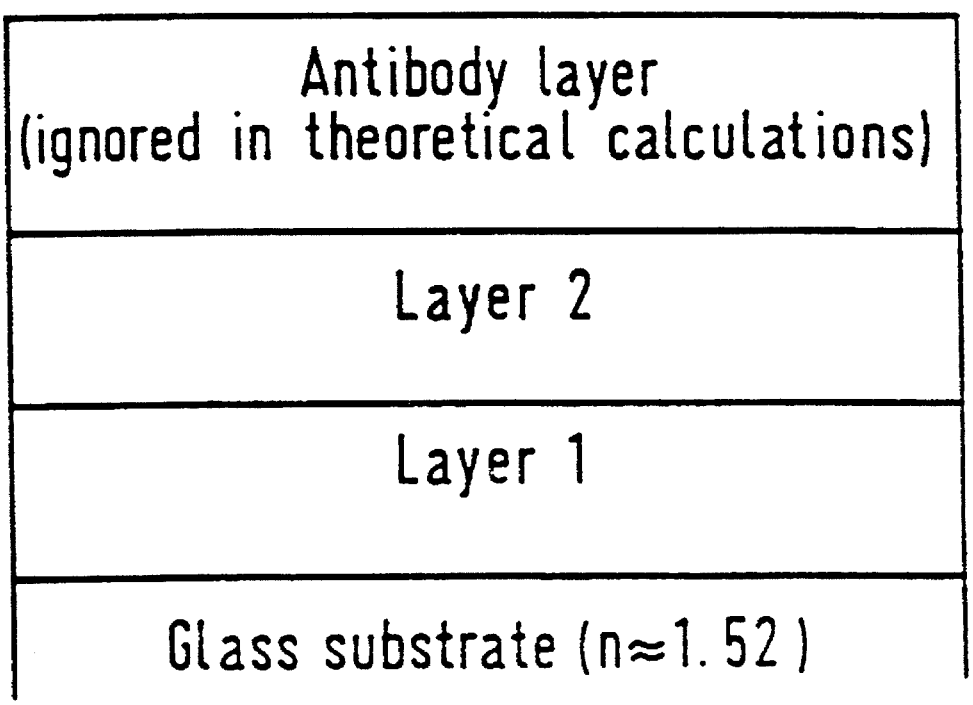
FIG. 1 schematically depicts an optical structure for use in the disclosed immunoassays.

Table 2 below shows a comparison of the results theoretically obtainable using an optical structure as depicted schematically in FIG. 1. The excitation wavelength for all mechanisms was 543 nm and the fluorophore was rhodamine B with a peak emission at 570 nm and a half width of 35 nm (from 555 nm to 590 nm).

Figure 2:
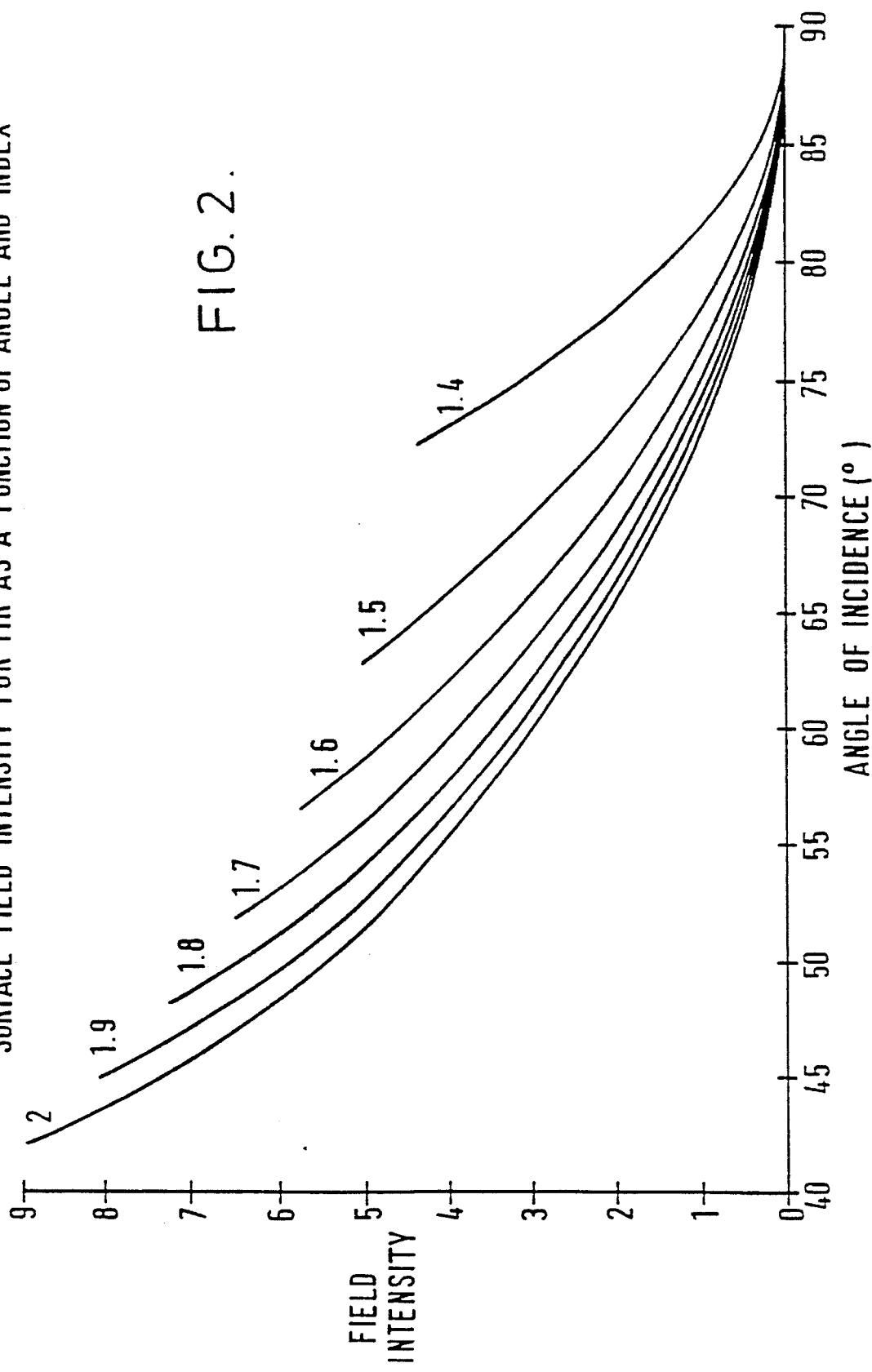
FIG. 2 shows the surface field intensity plotted as a function of angle for a number of glass indices in water.
Figure 3:
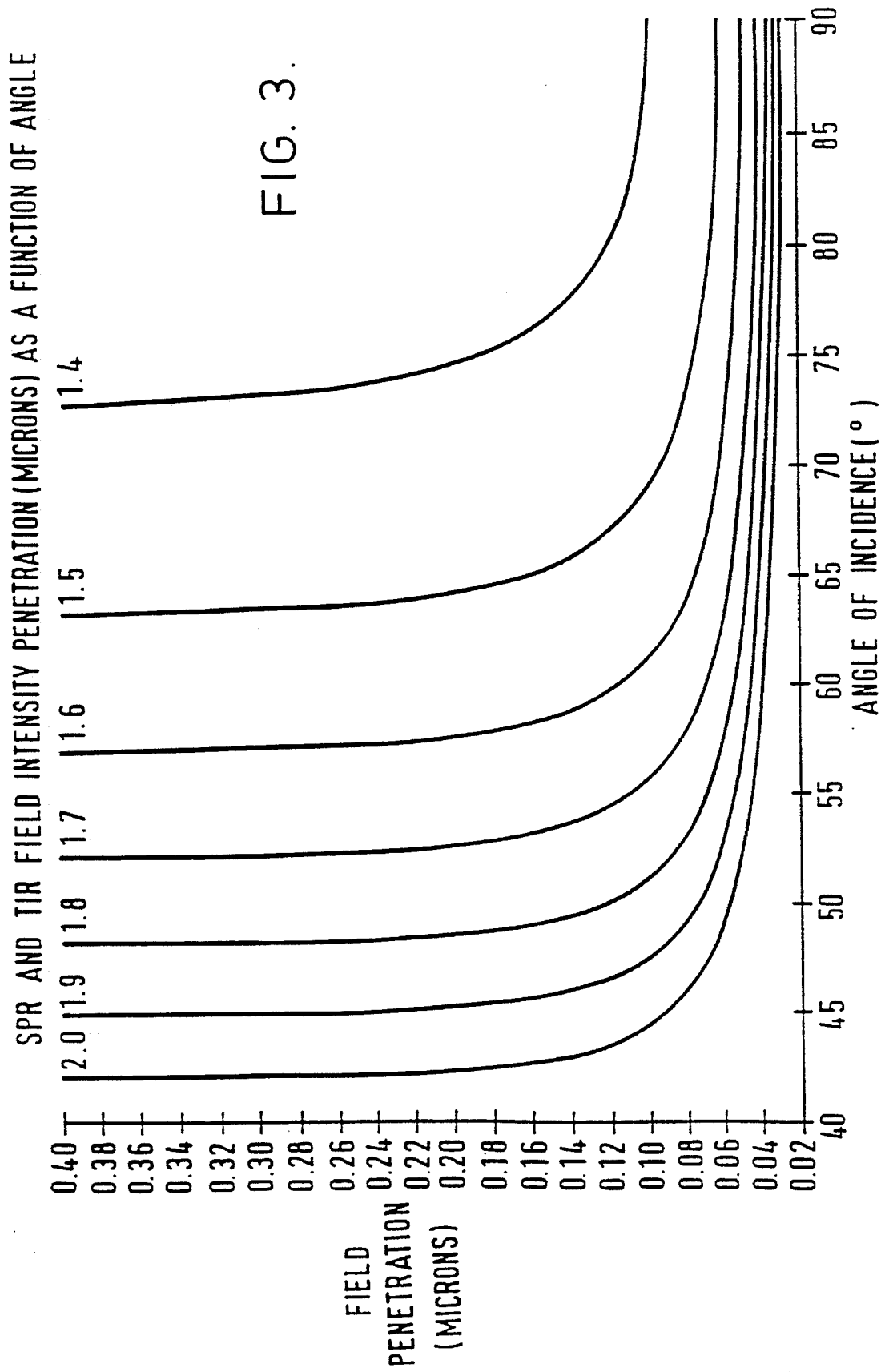
FIG. 3 shows the field intensity penetration plotted as a function of angle.

EXAMPLE 2 Total Internal Reflection a) FIG. 2 shows the surface field intensity plotted as a function of angle for a number of glass indices in water, with a wavelength of 543 nm (green HeNe laser). For a glass slide with a refractive index of 1.52 the field intensity is 2.5 times that of the incident radiation at 70°.

b) FIG. 3 shows the field intensity penetration plotted as a function of angle. Away from the critical angle this is a slowly varying function of the angle of incidence. For the example given in (a) above the field penetration is about 90 nm at 70°. It is not desirable to work too close to the critical angle because the penetration is too great and poor surface discrimination would result. Thus, a balance between field intensity and penetration depth must be struck.

EXAMPLE 3 Surface Plasmon Resonance

Figure 4:
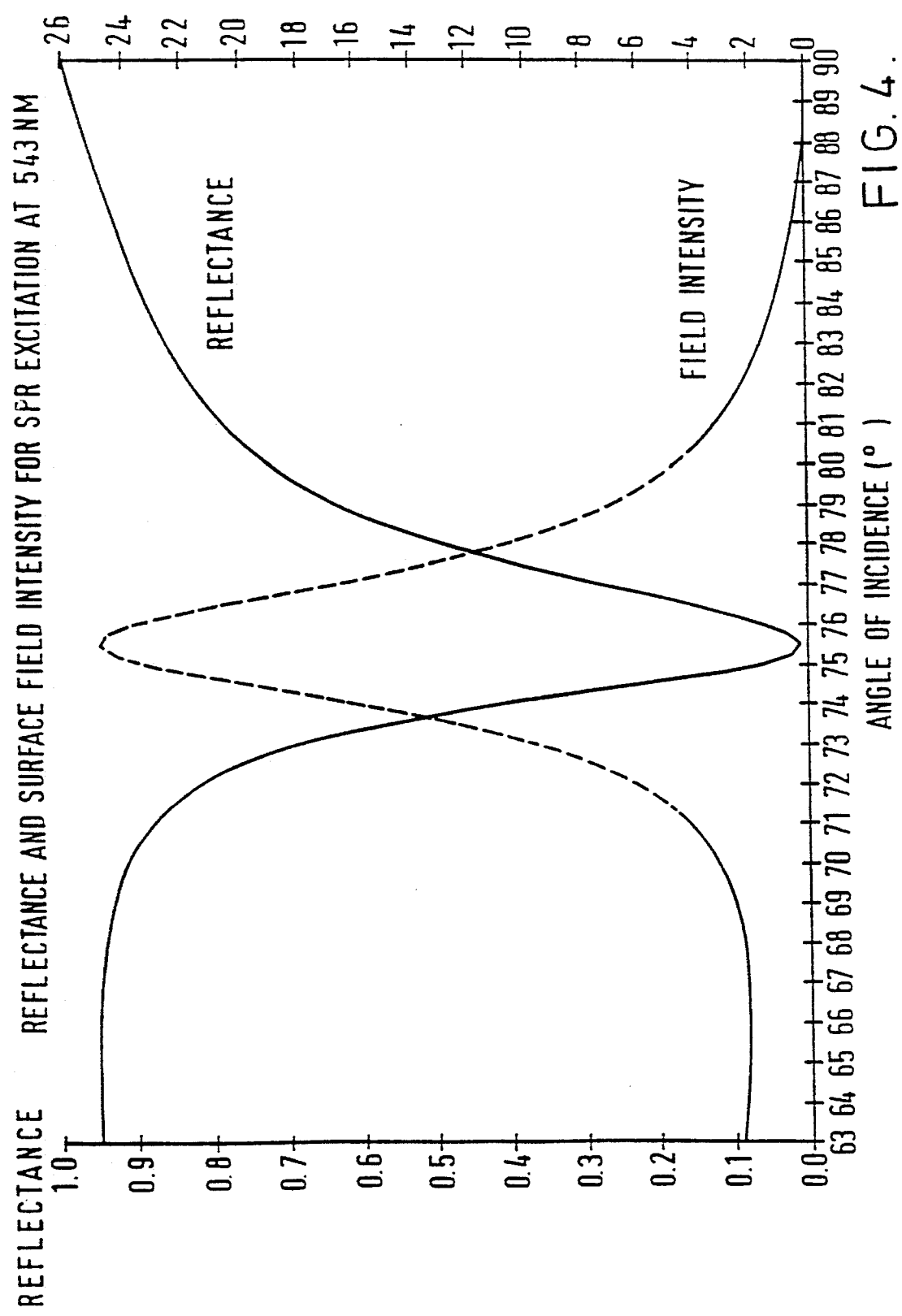
FIG. 4 shows the reflectance and surface field intensity of a 50 nm silver film in water.

FIG. 4 shows the reflectance and surface field intensity of a 50 nm silver film in water irradiated at 543 nm. A twenty-five-fold enhancement of the field intensity results when compared with the intensity of the incident radiation.

TABLE 2

| Mechanism | Layer 1 | Layer 2 | Excitation angle | Emission peak angle | Emission half width |
|---|---|---|---|---|---|
| SPR | Ag 50 nm | SiO$_2$ 10 nm | 72.80° | 70.72° | 1.92° |
| LRSPR | MgF$_2$ 1000 nm | Ag 26 nm | 65.67° | 65.31° | 0.39° |
| LRSPR | MgF$_2$ 500 nm | Ag 40 nm | 67.61° | 66.80° | 0.84° |

EXAMPLE 4 Comparison of SPR and Total Internal Reflection

Figure 5:
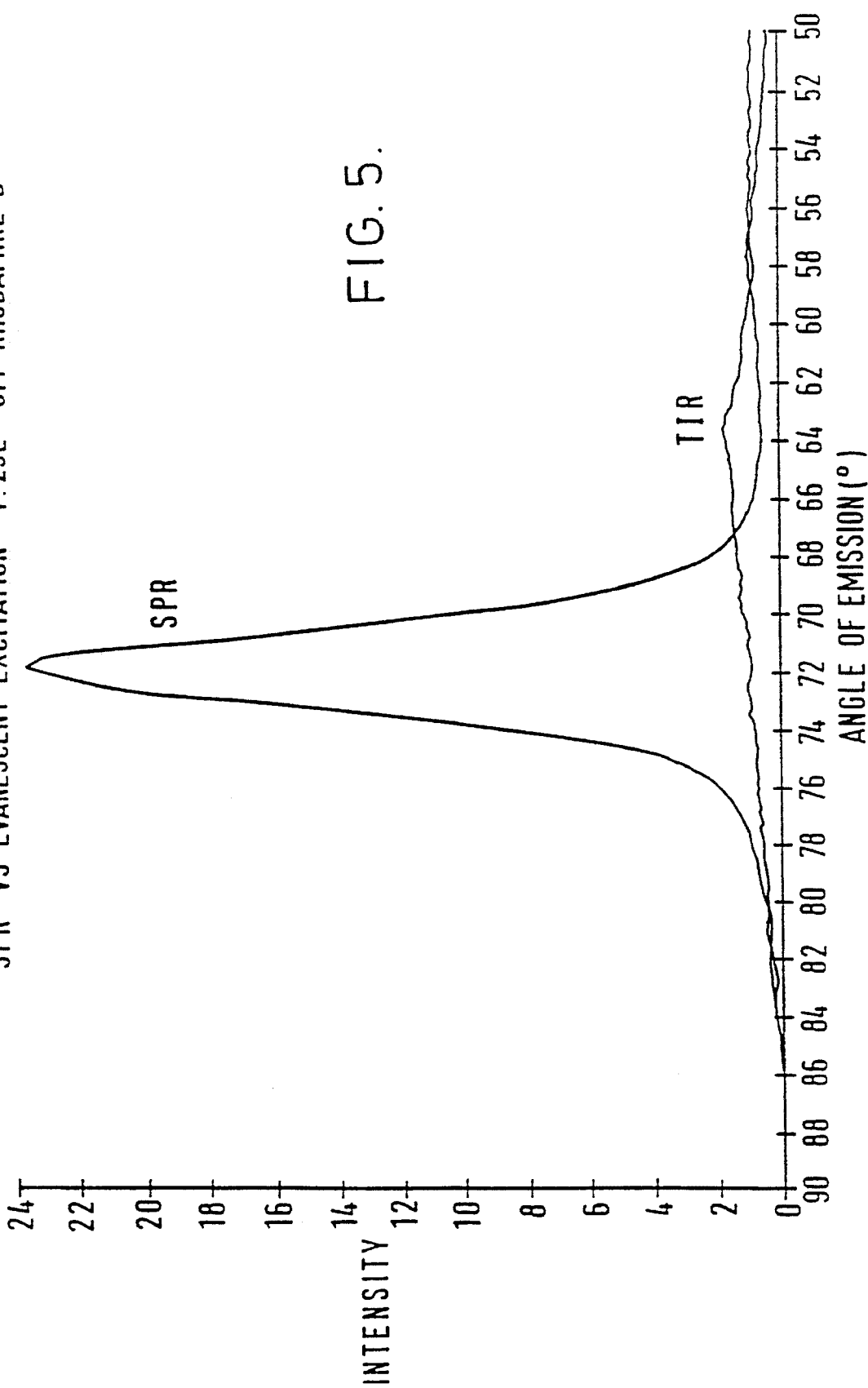
FIG. 5 shows a comparison of the excitation of rhodamine B solution surface plasmon resonance and total internal reflection.

FIG. 5 shows a comparison of the excitation of a rhodamine B solution by surface plasmon resonance and total internal reflection. The emission intensity enhancement and narrow emission range for the SPR geometry can be clearly seen. The experimental details follow.

(i) Fabrication of an Optical Structure

Glass slides measuring 25 mm×75 mm were cleaned ultrasonically in a solution of detergent. Using vacuum deposition, chromium was deposited onto one half of one surface of each slide through a mask, to a thickness of 1 nm. In the same way, silver was deposited onto the chromium layer to a thickness of 54 nm. The mask was removed and a 10 nm coating of silica was deposited onto the whole of said surface by similar means, to ensure that both halves of the surface of each slide had the same physico-chemical properties. The slides were washed with ultra-pure water. Each slide was scribed and cut into three pieces (such that each piece was half-silvered). Each piece was used to make a capillary cell using another piece of glass of similar size and double-sided adhesive tape.

(ii) Experimental Procedure

A sample solution was made up using an appropriate concentration of a suitable protein labelled with rhodamine B. The experimental set up was as described in section (iii) of Example 5, below.

EXAMPLE 5 Assay for Human Chorionic Gonadotrophin (hCG) Using an Indirect Surface Plasmon Resonance Technique (i) Fabrication of an Optical Structure Glass slides measuring 25 mm×75 mm were cleaned ultrasonically in a solution of detergent. Using vacuum deposition, aluminium was deposited onto one half of one surface of each slide through a mask, to a thickness of 1 nm. In the same way silver was deposited onto the aluminium layer to a thickness of 54 nm. The mask was removed and a 10 nm coating of silica was deposited onto the whole of said surface by similar means, to ensure that both halves of the surface of each slide had the same surface chemistry. The slides were suspended 5 mm above a pool of GOPS (glycidoxypropyltrimethoxysilane) for 2 hours at 20° C. in order to silanize the silica surface, following which the slides were baked at 60° C. for one hour. One 75 ul drop of a 20 ug/ml solution of α12/17 anti-hCG antibody in HEPES buffer was placed on each half of each slide, and the slides were left to dry for two hours. The slides were washed with ultra-pure water and then a solution of sucrose with tris(hydroxymethyl)aminomethane and sodium azide was deposited on the surface of the slide by means of spinning. Each slide was scribed and cut into three pieces (such that each piece was half-silvered). Each piece was used to make a capillary cell using another piece of glass of similar size and double-sided adhesive tape.

(ii) Assay Methodology

A sandwich-type assay was performed using premixed solutions in horse serum of hCG and XRITC-labelled antibody immobilised in the capillary cell. The concentration of XRITC-labelled antibody used was 2.5 ug/ml. Sample solutions were taken up by the capillary cells prepared as in section (i) and allowed to incubate for fifteen minutes before a reading was taken.

(iii) Experimental Set-up

The filled capillary cell under study was coupled to a hemicylindrical lens using a fluid of suitable refractive index. Light from a green helium-neon laser was then directed at the slide (i.e. the plate of the cell which carried the immobilised antibody) through the planar wall of the lens at an angle suitable for surface plasmon resonance to occur. Fluorescence emission was monitored by rotating a photomultiplier tube in a plane perpendicular to the plane of the incident/reflected light. The light reaching the PMT detector passed through a 610 nm bandpass filter to remove any scattered excitation light. A slit was placed behind the filter to give an angular resolution of 1°. Two lenses focussed the light passing through the slit onto the detector. A comparison of the fluorescence arising from surface plasmon resonance with that arising from total internal reflection was made by sliding the cell on the prism so that the silvered and unsilvered halves of the cell were interrogated in turn.

RESULTS

Figure 6:
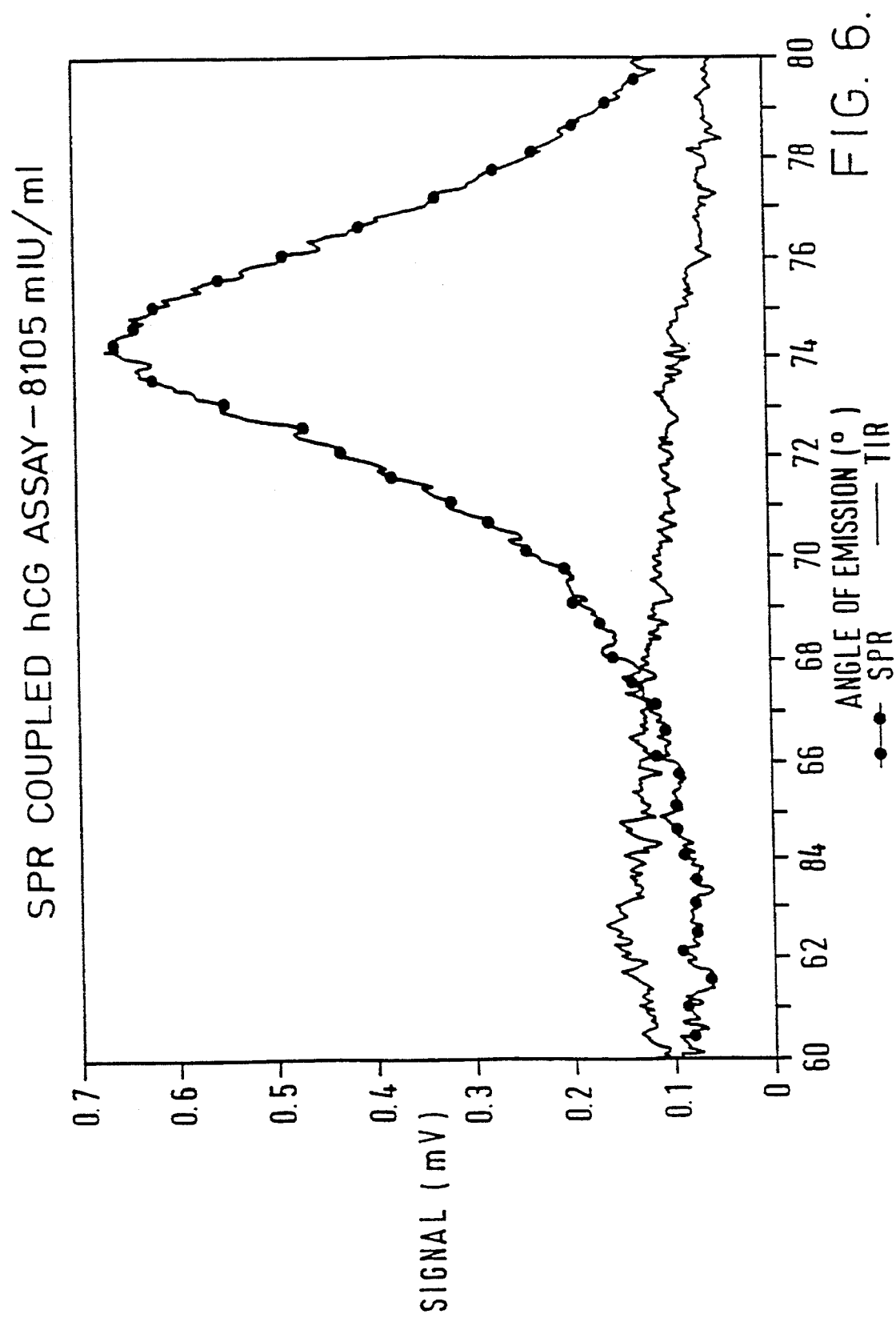
FIG. 6 shows a comparison of the signals obtained over an angular emission range from a capillary cell containing δ 105 mIU/ml hCG in serum, as obtained by SPR and TIR excitation.

FIG. 6 shows a comparison of the signals obtained over the angular emission range 60°–80° from a capillary cell containing 8105 mIU/ml hCG in serum, as obtained by SPR and TIR excitation. Particularly noticeable is the strong peak in signal around 74° for SPR excitation. The integrated signal between 70° and 78° is 5.2 times greater using SPR excitation than using TIR excitation. Optimisation of the metal layer and improved protein immobilisation techniques should enable greater enhancements to be achieved.

Figure 7:
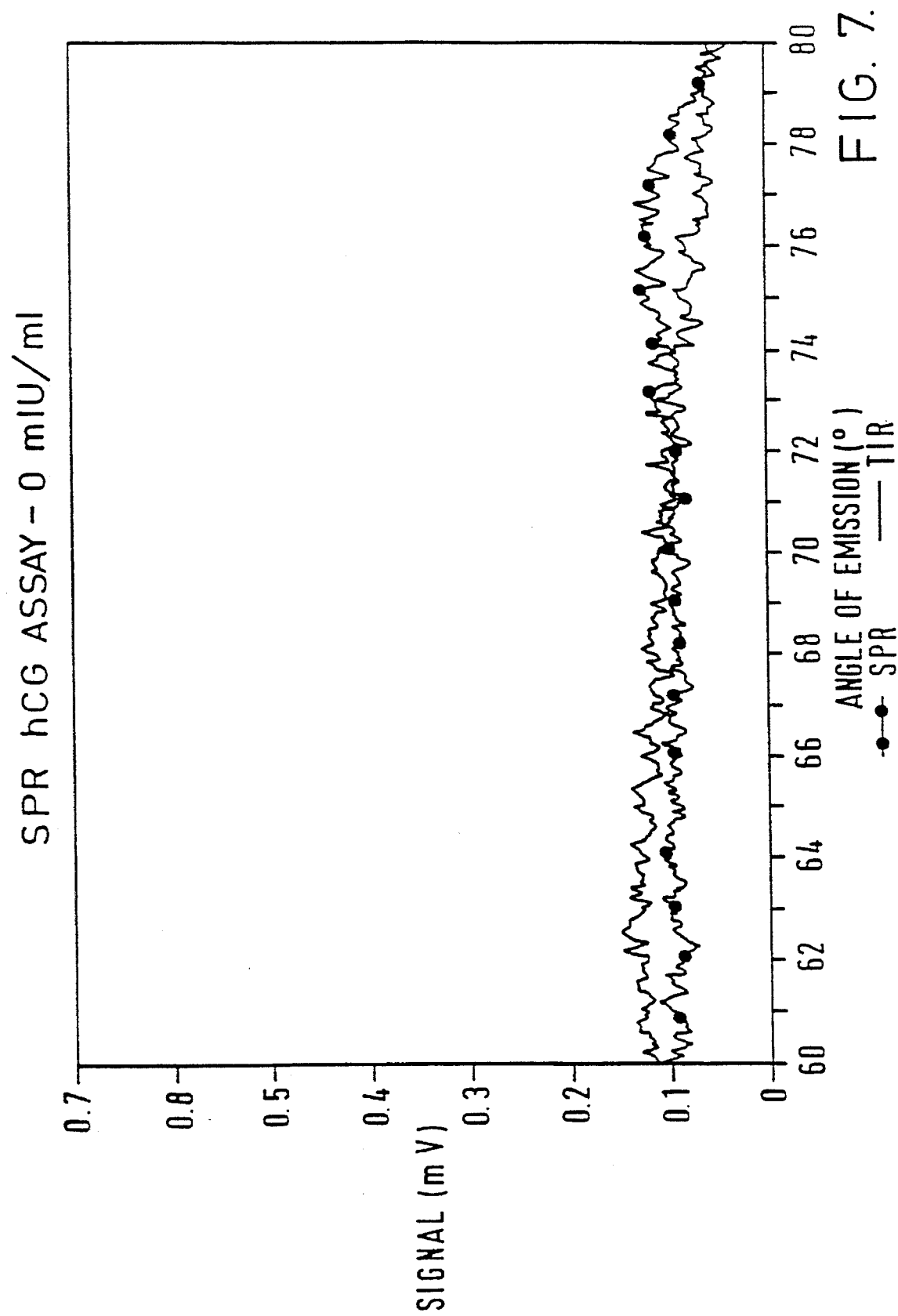
FIG. 7 shows a comparison of the signals obtained over an angular emission range from a capillary cell containing no hCG, as obtained by SPR and TIR excitation.

FIG. 7 shows signals over the same angular range, but this time from a cell filled with serum containing no hCG.

The emission resulting from SPR excitation shows a slight peak at 76° due to non-specific binding of the XRITC-labelled antibody.

EXAMPLE 6 —Demonstration of the Sensitivity of a Direct Guided Mode Sensor to Changes in Refractive Index.

(i) Fabrication of the Optical Structure

Glass microscope slides were cleaned ultrasonically in a detergent solution and extensively rinsed with ultrapure water. Using vacuum deposition techniques, a layer of aluminium, 1 nm thick, was deposited onto the surface of the glass followed by a film of silver, 54 nm thick. The silver surface was then coated with a glass film by spin coating a silica solgel (HT Products Inc., USA) onto the device at 300 rpm. The optical structures were baked overnight at 60° C. A capillary cell was fabricated from the optical structure and another piece of glass of the same dimensions using double sided adhesive tape.

(ii) Experimental Set-up

The filled capillary cell under study was optically coupled to a right angled crown glass prism using an appropriate fluid. The cell was illuminated through the glass substrate and onto the silver film with a TM polarised HeNe Laser, the reflected light intensity being measured with a photodiode device. The prism was rotated through a range of angles during the measurement. The cell was filled with ultrapure water (refractive index 1.3316) and the position of the reflectance minimum noted. Then ultrapure water was replaced by a 5% solution of sucrose (refractive index of 1.3382) and then by a 10% solution of sucrose (refractive index of 1.3450), the position of the minimum in reflected light intensity being measured in the presence of the sucrose solutions.

(iii) Results

Figure 8:
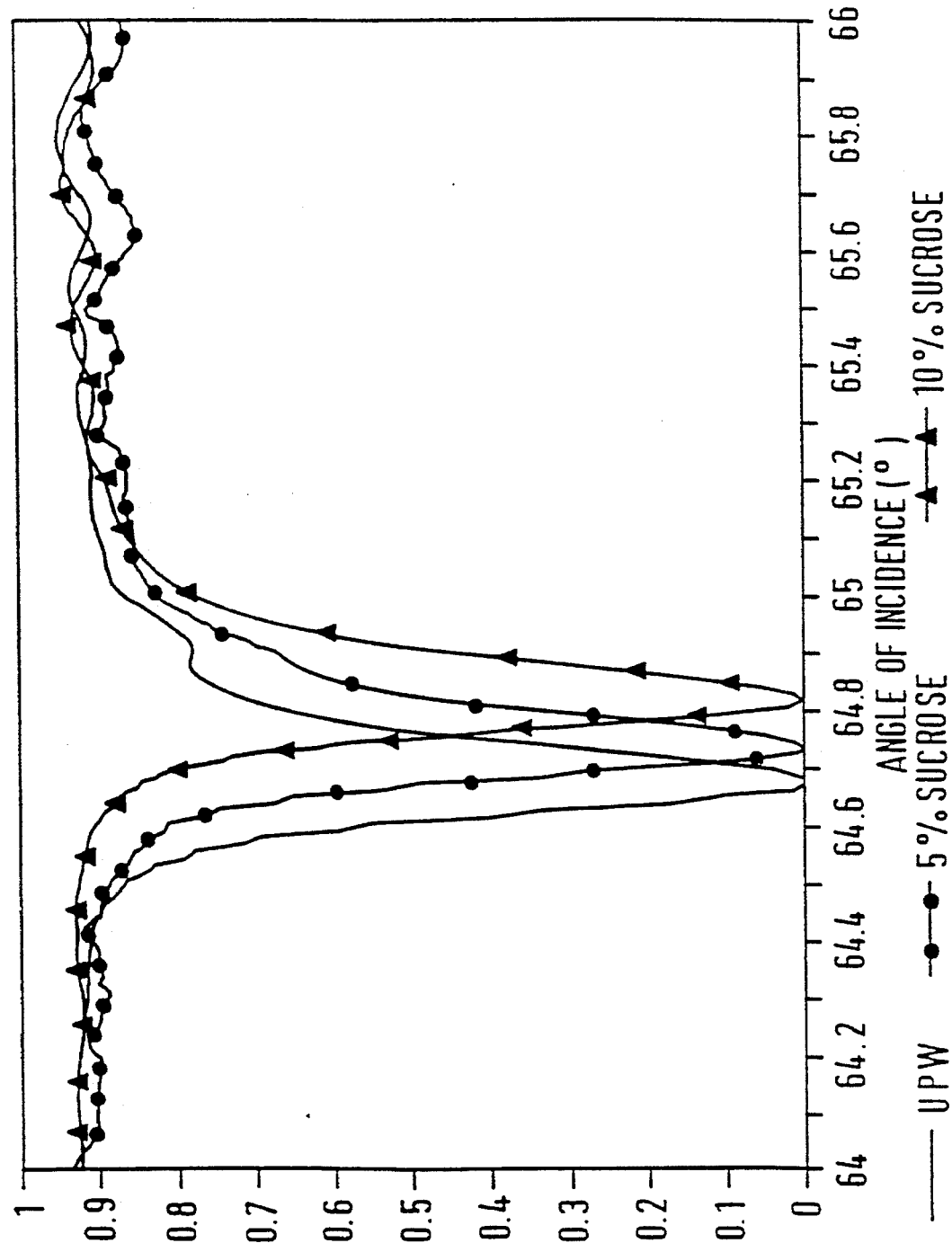
FIG. 8 shows the position of the minima in reflected light intensity of a guided mode light.

FIG. 8 shows the positions of the minima in reflected light intensity of the guided mode light in the optical structure. As the refractive index of the medium in contact with the optical structure increases there is a shift in the angle at which the minimum occurs, demonstrating that the device is sensitive to refractive index changes.

The binding of a ligand (e.g. an antigen) to an appropriate biological molecule (e.g. an antibody) immobilised on the device surface will result in a refractive index change. This will allow the guided mode sensor to be used as a direct optical immunosensor.

We claim:

1. A method of assaying for a ligand in a sample comprising forming a fluorescently or phosphorescently labelled complex of ligand or ligand analogue on a surface of an optical structure comprising in sequence a planar waveguide, a dielectric layer and a metal layer, said optical structure supporting long range surface plasmon resonance and carrying a specific binding partner for the ligand bound to the metal layer, irradiating said waveguide with excitation radiation sufficient to produce long range surface plasmon resonance which generates fluorescence or phosphorescence in said complex, said irradiation being at a suitable angle so as to produce a path of total internal reflection of said excitation radiation within said waveguide and monitoring the generated fluorescence or phosphorescence which emerges from said waveguide perpendicular to the path of said excitation radiation within said waveguide and not in the path of the excitation radiation.

2. The method of claim 1 wherein said metal layer is silver of 10 to 50 nm thick and said dielectric layer is magnesium fluoride of 10 to 2000 nm thick.

3. The method of claim 2 wherein said silver layer is 15.5 nm thick and said magnesium fluoride layer is 1500 nm thick.

4. In a method of assaying for a ligand in a sample comprising forming a fluorescently or phosphorescently labelled complex of ligand or ligand analogue on a surface of an optical structure carrying a specific binding partner for the ligand on a metal layer, said optical structure comprising a substrate with a metal layer capable of supporting surface plasmon resonance interposed between said substrate and said complex, irradiating another surface of said optical structure with excitation radiation at a suitable angle so as to produce surface plasmon resonance which generates fluorescence or phosphorescence in said complex, and monitoring the generated fluorescence or phosphorescence, the improvement wherein said optical structure has a dielectric layer interposed between said substrate and said metal layer so as to support long range surface plasmon resonance, and said excitation radiation produces long range surface plasmon resonance which generates fluorescence or phosphorescence in said complex.

5. The method of claim 4 wherein said metal layer is silver of 10 to 50 nm thick and said dielectric layer is magnesium fluoride of 10 to 2000 nm thick.

6. The method of claim 4 or 5 wherein said substrate is a planar waveguide.

7. In a method of assaying for a ligand in a sample comprising contacting the sample with a specific binding partner for the ligand disposed on a surface of an optical structure which supports one or more guided modes of radiation, irradiating another surface of said optical structure with excitation radiation at a suitable angle so as to produce resonant guided mode coupling, and monitoring changes in said resonant guided mode coupling as a result of ligand complex formation, the improvement wherein said optical structure comprises a substrate with a metal layer thereon and a dielectric layer capable of supporting the guided mode on said metal layer, said metal and dielectric layers interposed between said substrate and said specific binding partner, and coupling the radiation to a guided mode carried by the dielectric layer.

8. The method of claim 7 wherein said substrate is a planar waveguide.

9. The method of claim 7 wherein said metal layer is silver or gold and said dielectric layer is silica.

10. The method of claim 9 wherein said metal layer is silver of 50 nm thick and said dielectric layer is silica of 350 to 750 nm thick.

11. The method of claim 9 wherein said excitation radiation is collimated and polarized.

12. The method of claim 9 wherein said planar waveguide comprises one wall of a capillary cell for holding sample fluid therewithin.

13. The method of claim 9 wherein said excitation radiation produces surface plasmon resonance which generates fluorescence or phosphorescence in said complex.

14. The method of claim 13 wherein said metal layer is silver of 10 to 50 nm thick.

15. The method of claim 9 or 13 wherein said excitation radiation is collimated and polarized.

16. The method of claim 9 or 13 wherein said planar waveguide comprises one wall of a capillary cell for holding sample fluid therewithin.

* * * * *